United States Patent
Nakazawa

(10) Patent No.: US 9,642,594 B2
(45) Date of Patent: May 9, 2017

(54) BLOOD VESSEL DIAMETER MEASUREMENT DEVICE

(75) Inventor: Yusuke Nakazawa, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 907 days.

(21) Appl. No.: 13/267,333

(22) Filed: Oct. 6, 2011

(65) Prior Publication Data

US 2012/0095345 A1 Apr. 19, 2012

(30) Foreign Application Priority Data

Oct. 19, 2010 (JP) .................................. 2010-234551

(51) Int. Cl.
| | | |
|---|---|---|
| A61B 8/06 | (2006.01) | |
| A61B 8/08 | (2006.01) | |
| A61B 8/00 | (2006.01) | |
| G01B 17/00 | (2006.01) | |
| G01B 17/02 | (2006.01) | |
| A61B 5/00 | (2006.01) | |

(52) U.S. Cl.
CPC .......... *A61B 8/0891* (2013.01); *A61B 8/4444* (2013.01); *G01B 17/00* (2013.01); *G01B 17/02* (2013.01); *A61B 5/489* (2013.01)

(58) Field of Classification Search
CPC ..... A61B 5/489; A61B 8/0891; A61B 8/4444; A61K 38/00; A61K 38/47
See application file for complete search history.

(56) References Cited

U.S. PATENT DOCUMENTS

| | | | | |
|---|---|---|---|---|
| 4,811,740 | A | * | 3/1989 | Ikeda .................... G10K 11/341 600/437 |
| 7,429,244 | B2 | | 9/2008 | Kinouchi et al. |
| 2003/0009101 | A1 | * | 1/2003 | Sunagawa et al. ........... 600/437 |
| 2003/0216646 | A1 | * | 11/2003 | Angelsen ................. A61B 8/06 600/437 |
| 2006/0241427 | A1 | * | 10/2006 | Kinouchi et al. ............. 600/437 |
| 2012/0095345 | A1 | | 4/2012 | Nakazawa |

FOREIGN PATENT DOCUMENTS

| | | |
|---|---|---|
| JP | 2005-074146 A | 3/2005 |
| JP | 4441664 B2 | 3/2010 |
| JP | 2012-085789 A | 5/2012 |

* cited by examiner

*Primary Examiner* — Joseph M Santos Rodriguez
(74) *Attorney, Agent, or Firm* — Global IP Counselors, LLP

(57) ABSTRACT

A control part includes a transmission angle control unit that controls a transmission angle of ultrasonic waves transmitted from three ultrasonic arrays, a first reflected wave measuring unit that measures a first arrival time of a first reflected wave which is reflected by a blood vessel and is first to arrive at the ultrasonic arrays, a second reflected wave measuring unit that measures a second arrival time of a second reflected wave which arrives at the ultrasonic arrays after a predetermined time from the first arrival time, an outside diameter computation unit that computes an outside diameter of the blood vessel based on the first arrival time of three first reflected waves, and an inside diameter of the blood vessel computation unit that computes an inside diameter based on the second arrival time of three second reflected waves.

13 Claims, 10 Drawing Sheets

BLOOD VESSEL DIAMETER MEASUREMENT DEVICE

CROSS-REFERENCE TO RELATED APPLICATIONS

This application claims priority to Japanese Patent Application No. 2010-234551 filed on Oct. 19, 2010. The entire disclosure of Japanese Patent Application No. 2010-234551 is hereby incorporated herein by reference.

BACKGROUND

Technical Field

The present invention relates to a blood vessel diameter measurement device for measuring the diameter of a blood vessel in a living body by using ultrasonic waves.

Related Art

A conventional measurement device is known which measures the diameter of a blood vessel in a living body by using ultrasonic waves (see Japanese Patent No. 4441664, for example).

In this measurement device according to Japanese Patent No. 4441664, an ultrasonic probe is provided which is provided with a first array and a second array in a direction which intersects with the axial direction of a blood vessel. Each array has a plurality of ultrasonic elements. In each array, the plurality of ultrasonic elements transmits ultrasonic waves to the blood vessel so that the ultrasonic waves are parallel to each other, and receives the ultrasonic waves reflected by the blood vessel. The time from transmission to reception of the ultrasonic waves is measured, and the diameter of the blood vessel is computed based on the measured time.

SUMMARY

When ultrasonic waves are transmitted from the ultrasonic elements in the direction orthogonal to the wall surface of the blood vessel, the intensity of the ultrasonic waves reflected by the wall surface of the blood vessel is not reduced, and the ultrasonic elements can accurately receive the reflected ultrasonic waves. However, in a measurement device such as the one described in Japanese Patent No. 4441664, since the ultrasonic waves are transmitted to the wall surface of the blood vessel so as to be parallel to each other, the ultrasonic waves other than those that pass through the center of the blood vessel are transmitted without being orthogonal to the wall surface of the blood vessel. Therefore, of the ultrasonic waves transmitted not orthogonally to the wall surface of the blood vessel, the intensity of the ultrasonic waves reflected by the wall surface of the blood vessel decreases, and the ultrasonic elements are unable to accurately receive the reflected ultrasonic waves. An inaccurate measurement of the diameter of the blood vessel may therefore result.

In cases where the blood vessel wall has a small thickness, or the blood vessel is constricted, it is impossible to distinguish between reflected ultrasonic waves that are reflected by the inside wall or the outside wall, and it may therefore be impossible to accurately compute the diameter of the blood vessel.

An object of the present invention is to provide a blood vessel diameter measurement device whereby the diameter of a blood vessel can be accurately measured.

A blood vessel diameter measurement device according to a first aspect of the present invention includes at least three ultrasonic arrays and a control part. The ultrasonic arrays are arranged on a probe configured and arranged to touch a living body, each of the ultrasonic arrays having a linear array structure in which a plurality of ultrasonic elements are arranged in a single direction. The control part is configured to compute an outside diameter and an inside diameter of a blood vessel in the living body based on an arrival time between transmission of ultrasonic waves from the ultrasonic arrays and arrival of the ultrasonic waves at the ultrasonic arrays after the ultrasonic waves are reflected by the blood vessel. The control part includes a transmission angle control unit, a first reflected wave measuring unit, a second reflected wave measuring unit, an outside diameter computation unit, and an inside diameter computation unit. The transmission angle control unit is configured to control a transmission angle of the ultrasonic waves for each of the ultrasonic arrays. The first reflected wave measuring unit is configured to measure, for each of the ultrasonic arrays, a first arrival time of a first reflected wave which is received first among reflected waves of the ultrasonic waves reflected by the blood vessel, the ultrasonic waves being transmitted with the transmission angle thereof being controlled by the transmission angle control unit so that the ultrasonic waves pass through a center of the blood vessel. The second reflected wave measuring unit is configured to measure, for each of the ultrasonic arrays, a second arrival time of a second reflected wave which is received within a range of a predetermined time that is set based on the first arrival time. The outside diameter computation unit is configured to compute the outside diameter of the blood vessel based on the first arrival time for each of the ultrasonic arrays. The inside diameter computation unit is configured to compute the inside diameter of the blood vessel based on the second arrival time for each of the ultrasonic arrays.

According to this aspect, since a transmission angle control unit is provided for controlling the transmission angle of the ultrasonic waves so that the ultrasonic waves pass through the center of the blood vessel, ultrasonic waves can be reliably transmitted in the direction orthogonal to the wall surface of the blood vessel, the intensity of the reflected waves can be prevented from decreasing as in the conventional technique described above, and the reflected waves can be reliably received.

Moreover, a first reflected wave measuring unit is provided for measuring the first arrival time of the first reflected wave, for which the time from transmission of the ultrasonic waves to reception thereof is the shortest, and a second reflected wave measuring unit for measuring the second arrival time of the second reflected wave, which reaches the ultrasonic arrays within the range of a predetermined time that is set based on the first arrival time. Here, the first reflected wave is the ultrasonic wave that is reflected by the outside wall of the blood vessel, at the position closest to the ultrasonic arrays. The "second reflected wave which reaches the ultrasonic arrays within the range of a predetermined time" is a reflected wave that reaches the ultrasonic arrays within the range between the elapsing of the predicted time before reception of the wave next to be reflected by the inside wall of the blood vessel after the first reflected wave, and the predicted time before reception of the wave reflected by the outside wall of the blood vessel, farthest from the ultrasonic arrays.

It is thereby possible to eliminate reception of the wave next to be reflected by the inside wall of the blood vessel after the first reflected wave, and the wave reflected by the outside wall of the blood vessel, farthest from the ultrasonic arrays, and it is also possible to reliably receive the first reflected wave and the second reflected wave, which arrives a predetermined time later, distinctly from each other. Consequently, a desired reflection position of the ultrasonic waves in the blood vessel can be more accurately detected.

The outside diameter computation unit can also accurately compute the outside diameter of the blood vessel based on the coordinates of at least three reflection positions detected from the first arrival time of the first reflected wave. The inside diameter computation unit can also accurately compute the inside diameter of the blood vessel based on the coordinates of at least three reflection positions detected from the second arrival time of the second reflected wave.

In the blood vessel diameter measurement device according to a second aspect of the present invention, the control part preferably further includes a center position estimation unit configured to estimate a center position of the blood vessel based on a most-delayed arrival time of a most-delayed reflected wave among the reflected waves of the ultrasonic waves transmitted from at least two of the ultrasonic arrays at different transmission angles controlled by the transmission angle control unit and reflected by the blood vessel, and based on the transmission angle corresponding to the most-delayed reflected wave.

According to this aspect, the center position estimation unit estimates the center position of the blood vessel based on the latest arrival time of at least two reflected waves that reach the ultrasonic arrays latest among the ultrasonic waves transmitted from at least two ultrasonic arrays, and based on the transmission angles of the ultrasonic waves transmitted at this time. The processing speed can therefore be enhanced in comparison with a case in which three ultrasonic arrays are used to estimate the center position.

In the blood vessel diameter measurement device according to a third aspect, the second reflected wave measuring unit is preferably configured to determine whether there is at least one non-oscillation period of a reflected wave between the first reflected wave and the second reflected wave.

According to this aspect, since the second reflected wave measuring unit determines whether there is at least one non-oscillation period between the first reflected wave and the second reflected wave, it is possible to detect a reflected wave in which the first reflected wave and the second reflected wave are continuous, for example. Through this configuration, when the second reflected wave measuring unit detects that the reflected waves are continuous, by transmitting ultrasonic waves and measuring the reflected waves until the non-oscillation period is detected, the reflection position of the first reflected wave and the reflection position of the second reflected wave can be distinctly specified, and the diameter of the blood vessel can be accurately measured.

The blood vessel diameter measurement device according to a fourth aspect, the outside diameter computation unit is preferably further configured to compute center coordinates of the blood vessel based on coordinates of a reflection position of the first reflected wave for each of the ultrasonic arrays, the inside diameter computation unit is preferably further configured to compute the center coordinates of the blood vessel based on coordinates of a reflection position of the second reflected wave for each of the ultrasonic arrays, and the control part preferably further includes a warning output unit configured to determine whether an offset amount between the center coordinates computed by the outside diameter computation unit and the center coordinates computed by the inside diameter computation unit exceeds a predetermined threshold value, and to output a warning when the offset amount exceeds the threshold value.

In a case in which the blood vessel is constricted, or the shape of the blood vessel is no longer circular due to excessive contact of the probe with the body, the center coordinates computed by the outside diameter computation unit and the center coordinates computed by the inside diameter computation unit may differ from each other.

Therefore, in this aspect, a warning output unit is provided for comparing the offset amount of the center coordinates with a predetermined threshold value, and the warning output unit outputs a warning in the case that the offset amount exceeds the threshold value. Through this configuration, another measurement is performed after the user reattaches the probe in the test position after receiving the warning, and by performing this operation until the offset amount of the center coordinates is less than the threshold value, the center coordinates of the blood vessel can be calculated more accurately, and the diameter of the blood vessel can be accurately measured.

In the blood vessel diameter measurement device according to a fifth aspect, the control part preferably further includes a center position estimation unit configured to estimate a center position of the blood vessel based on a most-delayed arrival time of a most-delayed reflected wave among the reflected waves of the ultrasonic waves transmitted from at least two of the ultrasonic arrays at different transmission angles controlled by the transmission angle control unit and reflected by the blood vessel, and based on the transmission angle corresponding to the most-delayed reflected wave, and based on the transmission angle corresponding to the latest-arriving reflected wave, and a warning output unit configured to determine whether an offset amount between the center position of the blood vessel estimated by the center position estimation unit and the center coordinates computed by the outside diameter computation unit and the inside diameter computation unit exceeds a predetermined threshold value, and to output a warning when the offset amount exceeds the threshold value.

According to this aspect, the warning output unit compares the offset amount of the estimated center position of the blood vessel and the center coordinates computed by the outside diameter computation unit and the inside diameter computation unit, and outputs a warning in the case that the offset amount exceeds the threshold value. In this case, by reattaching the probe and performing another measurement, in the same manner as described above, the center coordinates of the blood vessel can be calculated more accurately, and the diameter of the blood vessel can be accurately measured.

BRIEF DESCRIPTION OF THE DRAWINGS

Referring now to the attached drawings which form a part of this original disclosure.

DETAILED DESCRIPTION OF EXEMPLARY EMBODIMENTS

An embodiment of the present invention will be described based on the accompanying drawings.

1. General Configuration of Blood Vessel Diameter Measurement Device

Figure 1:
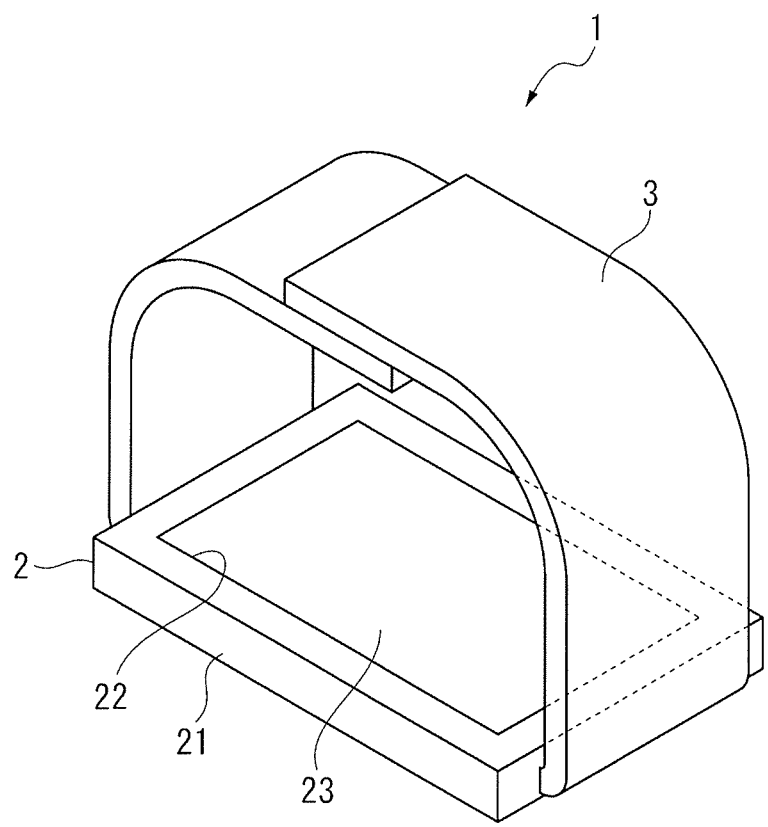
FIG. 1 is an external view showing the blood vessel diameter measurement device according to the present embodiment of the present invention.

FIG. 1 is an external view showing the blood vessel diameter measurement device 1 according to the present embodiment.

As shown in FIG. 1, the blood vessel diameter measurement device 1 is provided with a device body 2, and a band 3 for mounting the device body 2 to a human body or other living body. The blood vessel diameter measurement device 1 is mounted to the living body by tightening the band 3 in a state in which the living body is in contact with the back surface of the device body 2, and the blood vessel diameter measurement device 1 measures the outside diameter and inside diameter of a blood vessel in the living body.

2. Configuration of Device Body

As shown in FIG. 1, the device body 2 is provided with a rectangular housing 21, a sensor window 22 is formed on a back surface of the device body 2, and a probe 23 appressed to the living body is provided in the sensor window 22. The device body 2 is provided with a control part 4 (see FIG. 6) in addition to the probe 23.

As described above, the probe 23 is appressed to the living body during measurement of the outside diameter and inside diameter of a blood vessel in the living body by the blood vessel diameter measurement device 1.

Although not particularly shown in the drawings, an operating unit for operating the blood vessel diameter measurement device 1, a display unit for displaying measurement results, and other components are provided on the surface of the device body 2.

2-1. Configuration of Probe

Figure 2:
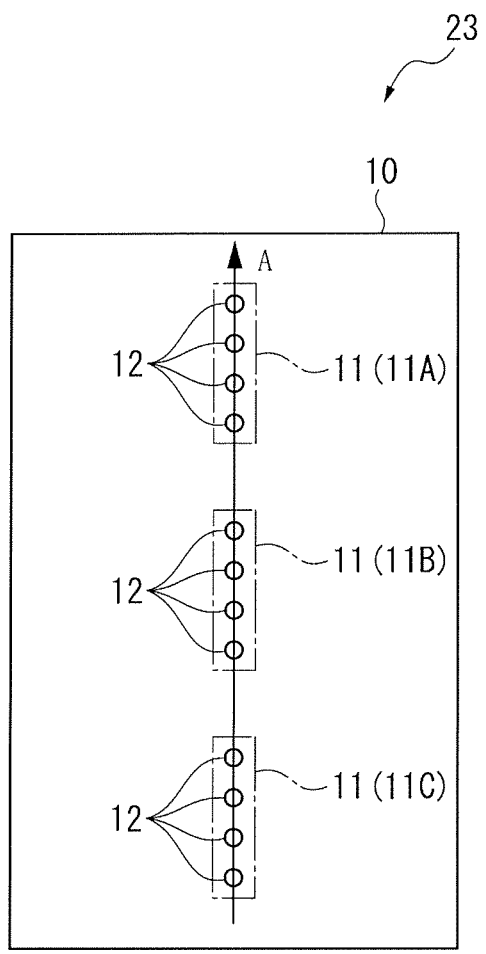
FIG. 2 is a plan view showing the general configuration of the probe according to the embodiment.

FIG. 2 is a plan view showing the general configuration of the probe 23 of the present embodiment.

As shown in FIG. 2, the probe 23 is provided with a rectangular substrate 10 formed of silicon (Si) or the like. Three ultrasonic arrays 11 (11A, 11B, 11C) are provided in the direction of the long side (the side on which the proximal end of the band 3 is not attached) of the substrate 10 so as to pass through the center position in the plane of the substrate 10. The ultrasonic arrays 11 are provided with a plurality of ultrasonic elements 12, and have a linear array structure (one-dimensional array structure) in which the plurality of ultrasonic elements 12 is aligned in a scanning direction A. During measurement of the blood vessel diameter, the probe 23 is appressed to the living body so that the arrangement direction of the ultrasonic elements 12 is orthogonal to the axial direction of the blood vessel.

Figure 3A:
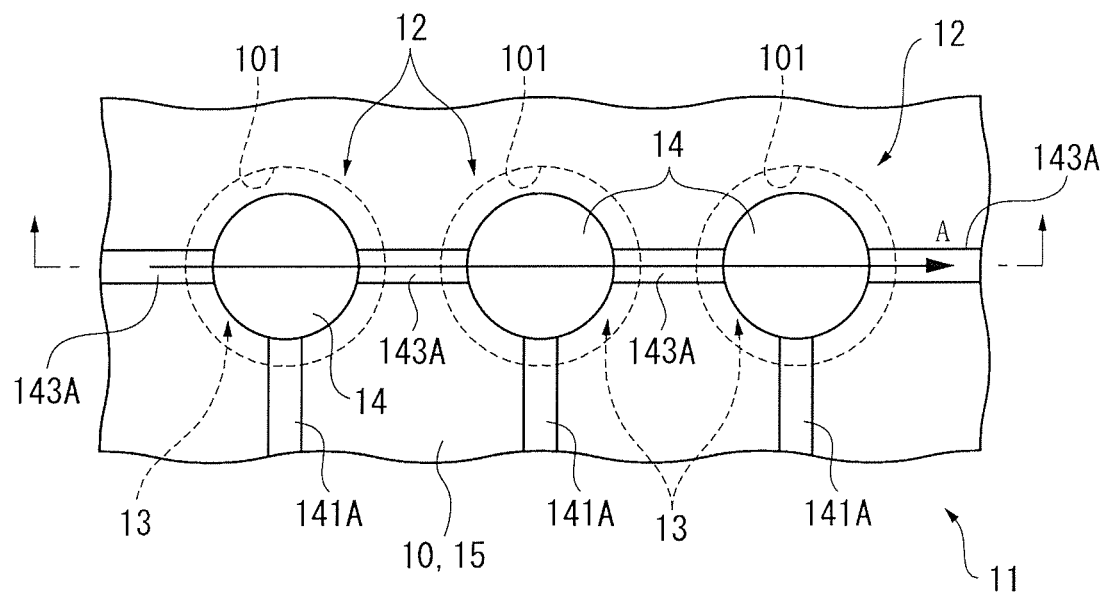
FIG. 3 is an enlarged plan view and a sectional view showing the ultrasonic arrays according to the embodiment.
Figure 3B:
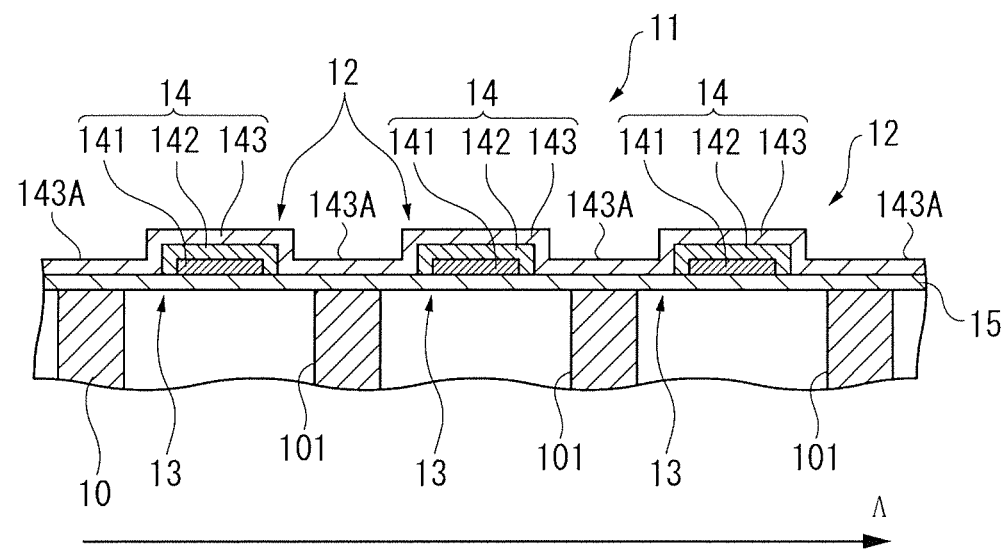

FIG. 3 is an enlarged plan view (FIG. 3A) and an enlarged sectional view (FIG. 3B) in which the ultrasonic arrays 11 are enlarged.

The ultrasonic elements 12 constituting each of the ultrasonic arrays 11 are provided with a diaphragm 13 and a piezoelectric body 14 formed on the diaphragm 13. The configuration of the diaphragm 13 and the piezoelectric body 14 is described hereinafter.

A plurality of open parts 101 circular in plan view is formed in the direction of the long side in the substrate 10. A support film 15 is laminated on the substrate 10, and the open parts 101 are blocked by the support film 15.

The support film 15 is composed of a two-layer structure which includes an $SiO_2$ film and a $ZrO_2$ layer. In the case that the substrate 10 is an Si substrate, the $SiO_2$ layer may be formed by subjecting the substrate surface to a thermal oxidation treatment. The $ZrO_2$ layer is formed on the $SiO_2$ layer by sputtering or another method.

The diaphragms 13 are composed of the regions of the support film 15 that block the open parts 101. The diaphragms 13 are exposed from the open parts 101 to the space in the ultrasonic wave output direction (the downward direction in FIG. 3) of the ultrasonic elements 12.

Each of the piezoelectric bodies 14 is provided with a lower electrode 141 laminated on top of the support film 15, a piezoelectric film 142 formed on the lower electrode 141, and an upper electrode 143 formed on the piezoelectric film 142.

As shown in FIG. 3A, lower electrode wires 141A extending in the direction orthogonal to the scanning direction A are connected on the support film 15 to the lower electrodes 141. The lower electrode wires 141A are provided independently to each of the ultrasonic elements 12.

Upper electrode wires 143A extending in the scanning direction A on the support film 15 are connected to the upper electrodes 143. The upper electrode wires 143A serve as common electrode wires in a single ultrasonic array 11. Specifically, the upper electrode wires 143A are connected to the upper electrode 143 of each adjacent ultrasonic element 12, and are connected to the GND, for example, at the ends thereof, as shown in FIG. 3. The upper electrodes 143 of the ultrasonic elements 12 are thereby grounded.

The piezoelectric films 142 are formed by films of PZT (lead zirconate titanate), for example. In the present embodiment, PZT is used for the piezoelectric films 142, but any material may be used insofar as the material is capable of contracting in the in-plane direction in response to application of a voltage, and lead titanate ($PbTiO_3$), lead zirconate ($PbZrO_3$), lead lanthanum titanate (($Pb,La)TiO_3$)), or the like may be used.

In the ultrasonic elements 12 thus configured, a voltage is applied to the lower electrodes 141 and the upper electrodes 143, and the piezoelectric films 142 thereby expand or contract in the in-plane direction. At this time, the surfaces on one side of the piezoelectric films 142 are joined to the support film 15 via the lower electrodes 141, and although the upper electrodes 143 are formed on the other surfaces of the piezoelectric films 142, since no other layers are laminated on the upper electrodes 143, the support film 15 sides of the piezoelectric films 142 do not readily expand and contract, the upper electrode 143 sides easily expand and contract. Therefore, when a voltage is applied to the piezoelectric films 142, convex flexure toward the open parts 101 occurs, and the diaphragms 13 are flexed. Consequently, by applying an alternating-current voltage to the piezoelectric films 142, the diaphragms 13 are made to vibrate with respect to the film thickness direction, and ultrasonic waves are transmitted by the vibration of the diaphragms 13.

In the case that ultrasonic waves are transmitted by the ultrasonic elements 12, when the ultrasonic waves are inputted to the diaphragms 13, the diaphragms 13 vibrate in the film thickness direction. In the ultrasonic elements 12, the vibration of the diaphragms 13 produces a potential difference between the surfaces of the piezoelectric films 142 on the side of the lower electrodes 141 and the surfaces of the piezoelectric films 142 on the side of the upper electrodes 143, and a reception signal (current) is outputted which is in accordance with the amount of displacement of the piezoelectric films 142 from the upper electrodes 143 and the lower electrodes 141.

Figure 4:
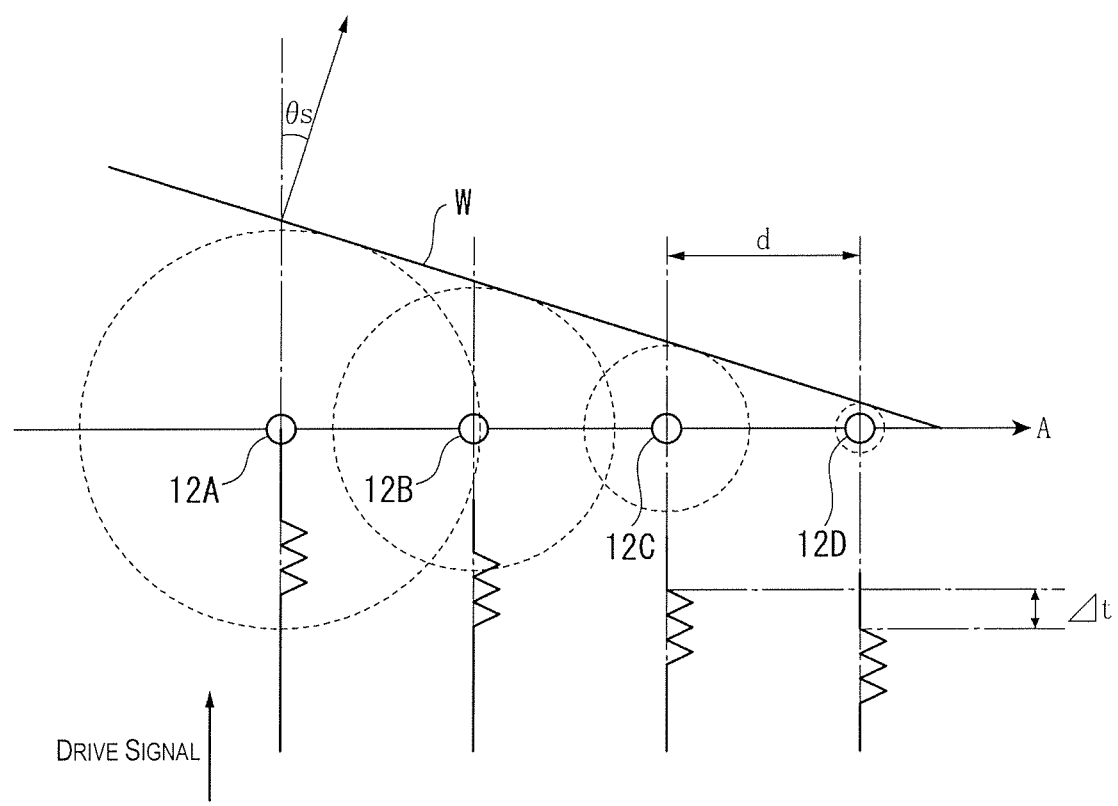
FIG. 4 is a view showing the transmission angle of the ultrasonic waves when the drive signal inputted to the ultrasonic elements of the embodiment is inputted at a sequential delay of $\Delta t$.

FIG. 4 is a view showing the transmission direction (transmission angle) of the ultrasonic waves when the drive signal inputted to the ultrasonic elements 12A through 12D is inputted at a sequential delay of Δt.

In an ultrasonic array 11 in which a plurality of ultrasonic elements 12 is arranged in the scanning direction A in the present embodiment, an ultrasonic plane wave can be transmitted in the desired direction by delaying and staggering the timing at which ultrasonic waves are transmitted from the ultrasonic elements 12.

When ultrasonic waves are transmitted from the ultrasonic elements 12, a synthetic wavefront W in which the ultrasonic waves strengthen each other is formed and propagated. As shown in FIG. 4, when the drive signal inputted to the ultrasonic elements 12A through 12D at an arrangement interval of d is delayed by Δt, the wavefront of an ultrasonic wave transmitted from the ultrasonic element 12 to which the drive signal is inputted first, and the wavefront transmitted from an ultrasonic element 12 to which the drive signal is subsequently inputted have different phases, and the synthetic wavefront W is propagated at an angle with respect to the scanning direction A.

At this time, the relationship indicated by Equation (1) is established, where $\theta_s$ is the transmission angle between the propagation direction of the synthetic wavefront W and the direction orthogonal to the scanning direction A, and c is the acoustic velocity.

Equation (1)

$$\Delta t = \frac{d \sin \theta_s}{c} \quad (1)$$

Figure 5:
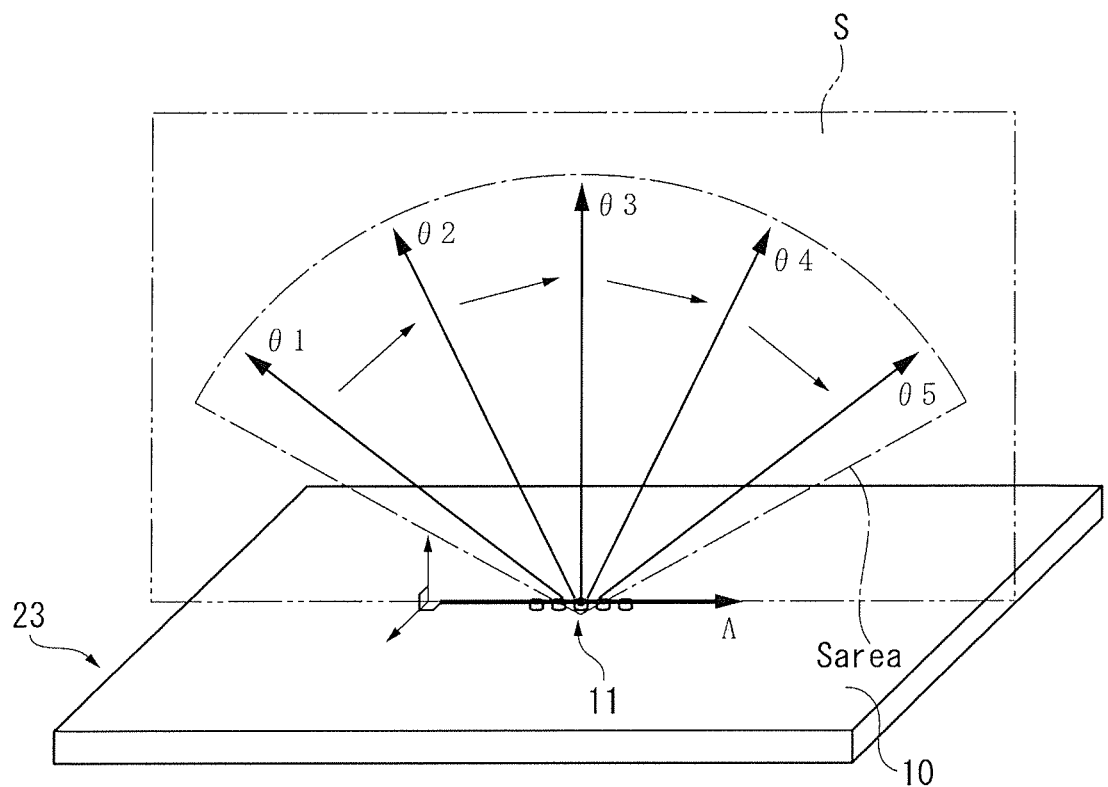
FIG. 5 is a view showing the scan area of the ultrasonic arrays of the embodiment.

FIG. 5 is a view showing the scan area Sarea of a single ultrasonic array 11.

As described above, the transmission angle of the ultrasonic waves can be varied by delaying the timing of the drive signal inputted to the ultrasonic elements 12 in the ultrasonic array 11. Here, since the ultrasonic array 11 has a linear array structure (one-dimensional array structure), the transmission angles of the ultrasonic waves are limited by a scan plane S which runs along the scanning direction A and is orthogonal to the substrate 10, as shown in FIG. 5, and the transmission angles cannot be varied in directions which intersect with the scan plane S. The scan area Sarea of the ultrasonic array 11 is thereby formed along the scanning direction A within the scan plane S orthogonal to the substrate 10. When the probe 23 is appressed to the living body so that the blood vessel passes through the scan area Sarea, ultrasonic waves are transmitted from the ultrasonic array 11 to the scan area Sarea, and the ultrasonic waves reflected by the blood vessel are received. The intersection between the blood vessel and the scan area Sarea can thereby be detected.

2-2. Configuration of Control Unit

Figure 6:
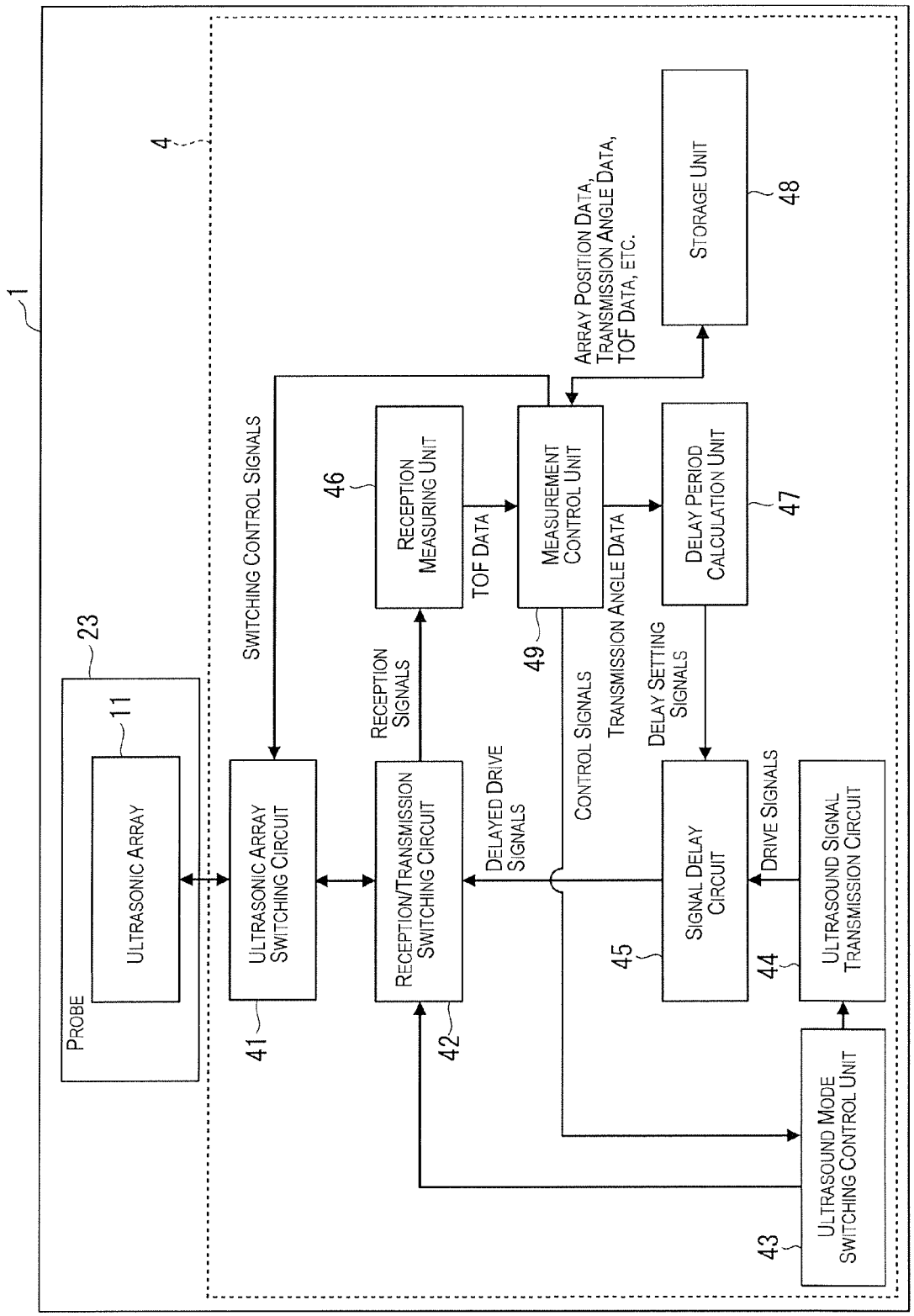
FIG. 6 is a block diagram showing the general configuration of the blood vessel diameter measurement device of the embodiment.

FIG. 6 is a block diagram showing the general configuration of the blood vessel diameter measurement device 1 of the present embodiment.

The control part 4 is provided with an ultrasonic array switching circuit 41, a reception/transmission switching circuit 42, an ultrasound mode switching control unit 43, an ultrasound signal transmission circuit 44, a signal delay circuit 45 (transmission angle control unit), a reception measuring unit 46 (first reflected wave measuring unit, second reflected wave measuring unit), a delay period calculation unit 47, a storage unit 48, and a measurement control unit 49.

The ultrasonic array switching circuit 41 is a switching circuit for switching the ultrasonic array 11 that is driven among the three ultrasonic arrays 11 provided to the probe 23.

In the blood vessel diameter measurement device 1 of the present embodiment, while ultrasonic waves are being received and transmitted from one ultrasonic array 11, outputting of drive signals to the other ultrasonic arrays 11 and reception of reception signals from the other ultrasonic arrays 11 are not performed. It is thereby possible to prevent ultrasonic waves transmitted from another ultrasonic array 11 from being received by the ultrasonic array 11 that is to be driven, and to prevent problems such as detection of noise or detection of reception signals from ultrasonic arrays 11 other than the ultrasonic array 11 that is to be driven.

The ultrasonic array switching circuit 41 is provided with a terminal group connected to the lower electrode wires 141A and the upper electrode wires 143A of the ultrasonic arrays 11, for example, and based on a switching control signal inputted from the measurement control unit 49 in order to switch to an array, the ultrasonic array switching circuit 41 connects the reception/transmission switching circuit 42 and the terminal group that corresponds to the ultrasonic array 11 indicated by the switching control signal. A configuration may also be adopted in which driving of a terminal group that corresponds to an ultrasonic array 11 not to be driven is withdrawn by connecting both the lower electrode wires 141A and the upper electrode wires 143A to GND, for example.

The reception/transmission switching circuit 42 is a switching circuit for switching the connection state based on a mode switching signal inputted from the ultrasound mode switching control unit 43.

Specifically, in the case that a control signal indicating a switch to the ultrasonic wave transmission mode is inputted from the ultrasound mode switching control unit 43, the reception/transmission switching circuit 42 switches to a connection state whereby the drive signal inputted from the signal delay circuit 45 can be outputted to the ultrasonic array switching circuit 41. In the case that a control signal indicating a switch to the ultrasonic wave reception mode is inputted from the ultrasound mode switching control unit 43, the reception/transmission switching circuit 42 switches to a connection state whereby the reception signal inputted from the ultrasonic array switching circuit 41 can be outputted to the reception measuring unit 46.

The ultrasound mode switching control unit 43 switches between an ultrasonic wave transmission mode for transmitting ultrasonic waves from the ultrasonic arrays 11, and an ultrasonic wave reception mode for receiving ultrasonic waves in the ultrasonic arrays 11.

Specifically, when a control signal indicating the start of blood vessel diameter measurement is inputted from the measurement control unit 49, the ultrasound mode switching control unit 43 first performs processing for switching to the ultrasonic wave transmission mode. In this processing, the ultrasound mode switching control unit 43 outputs a control signal indicating a switch to the transmission mode to the reception/transmission switching circuit 42, and outputs a control signal indicating the outputting of a drive signal from the ultrasound signal transmission circuit 44.

The ultrasound mode switching control unit 43 also recognizes a time counted by a clock unit (timer) not shown in the drawing, and performs processing for switching to the ultrasonic wave reception mode after a predetermined transmission time has elapsed from the ultrasonic wave transmission mode. The transmission time here may be set to approximately the time for which a burst wave of 1 to 2 frequencies, for example, is transmitted from the ultrasonic arrays 11. In the reception mode, the ultrasound mode switching control unit 43 outputs a control signal indicating a switch to the reception mode to the reception/transmission switching circuit 42, and causes the reception/transmission switching circuit 42 to switch to a connection state whereby the reception signal inputted from the ultrasonic arrays 11 can be inputted to the reception measuring unit 46.

In the ultrasound mode switching control unit 43, the processing described above is performed, for example, a pre-set number of times. This number of times is appropriately set according to the set number of transmission angles of ultrasonic waves. For example, as shown in FIG. 5, the processing described above is repeated five times in a case in which the transmission angle of the ultrasonic waves is switched to five levels to estimate the center position of the blood vessel.

In the transmission mode, when a control signal indicating the outputting of a drive signal from the ultrasound mode switching control unit 43 is inputted, the ultrasound signal transmission circuit 44 outputs a drive signal (drive voltage) for driving the ultrasonic elements 12 of the ultrasonic arrays 11 to the signal delay circuit 45.

When the drive signal for the ultrasonic elements 12 is inputted from the ultrasound signal transmission circuit 44, the signal delay circuit 45 delays the drive signal and outputs the delayed drive signal to the reception/transmission switching circuit 42.

The signal delay circuit 45 outputs a delayed drive signal in which the drive signal for driving the ultrasonic elements 12 is delayed Δt a time to the reception/transmission switching circuit 42, based on a delay setting signal inputted from the delay period calculation unit 47.

Figure 7:
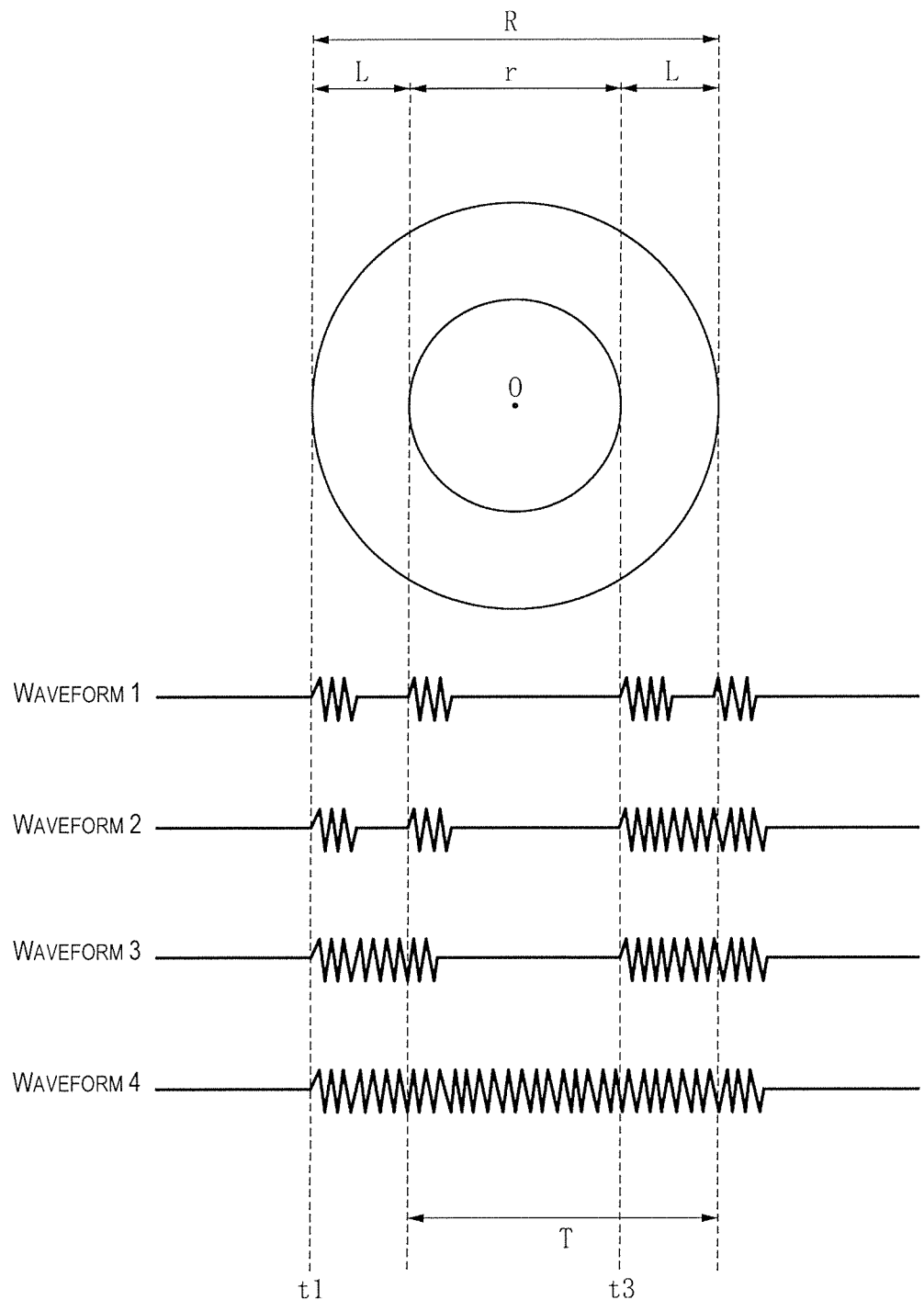
FIG. 7 is a view showing reflected waves of the ultrasonic waves transmitted from the ultrasonic array of the embodiment.

FIG. 7 is a view showing reflected waves of the ultrasonic waves transmitted from the ultrasonic arrays 11.

Figure 8:
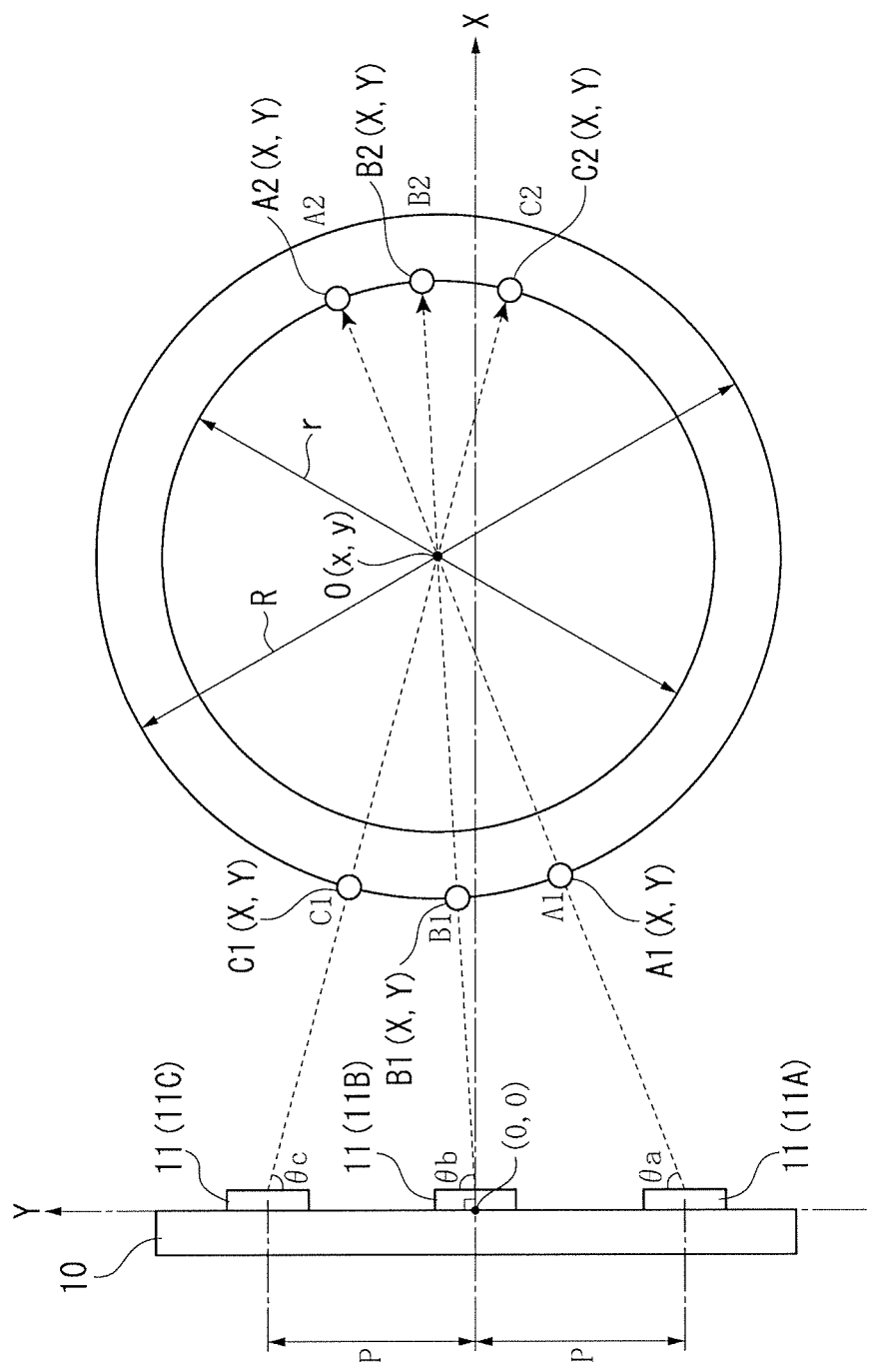
FIG. 8 is a schematic view showing ultrasonic waves from the ultrasonic arrays of the embodiment passing through the center position of the blood vessel.

FIG. 8 is a schematic view showing ultrasonic waves passing through the center position of the blood vessel from the ultrasonic arrays 11.

The reception measuring unit 46 monitors the time measured by the clock unit and measures the time until an ultrasonic wave is received.

Specifically, the reception measuring unit 46 monitors the timing at which the ultrasound mode switching control unit 43 performs the processing for switching to the transmission mode, i.e., the time since the time counted by the clock unit was reset by the ultrasound mode switching control unit 43. When the ultrasound mode switching control unit 43 performs the processing for switching to the reception mode, and the reception signal corresponding to the reflected ultrasonic waves received by the ultrasonic arrays 11 is inputted from the reception/transmission switching circuit 42 to the reception measuring unit 46, the reception measuring unit 46 acquires the time at the timing of the inputting (TOF data: time of flight data), and inputs the TOF data to the measurement control unit 49.

The reception measuring unit 46 acquires two sets of TOF data of the reception signal for which inputting is last to be completed among the reception signals of the reflected waves transmitted for each transmission angle (e.g., the transmission angles θ1 through θ5 shown in FIG. 5) from two ultrasonic arrays 11 and reflected by the blood vessel. The reception signal for which inputting to the reception measuring unit 46 is last to be completed is the reception signal of the reflected wave at the reflection position farthest from an ultrasonic array 11.

The reception measuring unit 46 also acquires the TOF data of time t1 (first arrival time of the present invention) at which the reception signal of the first wave (first reflected wave of the present invention) of reflected waves is inputted, and of time t3 (second arrival time of the present invention) at which the reception signal of the third wave (second reflected wave of the present invention) of the reflected waves is inputted, of the ultrasonic waves transmitted at a transmission angle in the reception signal, as shown in FIG. 7. The TOF data are also acquired for the first and third waves of reflected waves of the ultrasonic waves transmitted based on a transmission angle θs from the remaining ultrasonic arrays 11, the transmission angle θs being computed by a center position estimation unit 491 described hereinafter.

Patterns in which reception signals are received by the reception measuring unit 46 include the patterns of waveforms 1 through 4 shown in FIG. 7. In FIG. 7, the blood vessel is shown as having a circular shape, for the sake of convenience.

For example, in waveform 1, the reflected waves from the inside wall and outside wall of the blood vessel are acquired in ideal fashion, whereas in waveform 2, deformation of the blood vessel into an elliptical or other shape due to contraction or the like causes the reflected waves to be such that the third and fourth waves are continuous. In waveform 3, the reflected waves are such that the first and second waves are continuous, and the third and fourth waves are continuous, due to such factors as an extremely low wall thickness of the blood vessel. In waveform 4, the reflected waves are such that the first through fourth waves are continuous, due to significant contraction of the blood vessel in comparison with the case of waveform 2 or waveform 3, and extremely low wall thickness of the blood vessel.

It is therefore necessary, particularly in the patterns of waveform 1 and waveform 2, for the reception measuring unit 46 to receive the reception signal of the third wave distinctly from the reception signals of the second wave and the fourth wave. Therefore, when the condition is satisfied that the time t3 at which the reception signal of the reflected wave of the third wave is inputted is within the range of the predetermined time T of Equation (2) below, the reception signals of the second wave and the fourth wave are not received, and only the reception signal of the third wave can be received.

Equation (2)

$$\frac{2L \times 10^{-3}}{c} < T < \frac{2R \times 10^{-3}}{c} \qquad (2)$$

Here, R is the outside diameter of the blood vessel, and c is the acoustic velocity. Also, L is the wall thickness dimension of the blood vessel, and is calculated by L=(R−r)/2, where r is the inside diameter of the blood vessel. In general, since the inside diameter r is 1 (mm) and the outside diameter R is 3 (mm), the wall thickness dimension L is 1 (mm). Since the acoustic velocity c is 1530 (m/s), substituting these values into Equation (2) above gives the following relationship: 1300 (ns)<T<3920 (ns).

The reception measuring unit 46 also detects whether there is a single non-oscillation period between reception of the reception signal of the first wave and the reception signal of the third wave in FIG. 7. Specifically, the reception measuring unit 46 receives the reception signal of the first wave, detects the presence of a non-oscillation period before reception of the reception signal of the third wave, and determines that noise or other effects are absent when there is at least one non-oscillation period. In the case that there is no non-oscillation period, the reception measuring unit 46 determines that noise or other effects are present, inputs a re-measurement signal to the measurement control unit 49, and causes a control signal to be inputted from the measurement control unit 49 to the ultrasound mode switching control unit 43.

For example, in the pattern of waveform 1 in FIG. 7, after the reception signal of the first wave is received, a non-oscillation period occurs before the second wave, a non-oscillation period also occurs before the third wave, and another non-oscillation period occurs before the reception signal of the fourth wave is received. Non-oscillation periods therefore occur in three places. In the pattern of waveform 2 in FIG. 7, after the reception signal of the first wave is received, a non-oscillation period occurs before the second wave, and another non-oscillation period occurs before the reception signal of the third wave is received. Non-oscillation periods therefore occur in two places. In the pattern of waveform 3 in FIG. 7, after the reception signal of the first wave is received, a non-oscillation period occurs before the reception signal of the third wave is received. A non-oscillation period therefore occurs in one place. However, in the pattern of waveform 4 in FIG. 7, after the reception signal of the first wave is received, the reflected waves are continuous, and reception signals continue to be received. There is therefore no non-oscillation period, and a noise effect is determined to be present.

The delay period calculation unit 47 computes the drive delay time of the ultrasonic elements 12 based on transmission angle data inputted from the measurement control unit 49.

Here, the transmission angle data are data stored in advance in the storage unit 48, and in the present embodiment, for example, a configuration is described in which five items of transmission angle data θs=θ1 through θ5, as shown in FIG. 5, are stored in advance. A configuration may also be adopted in which six or more items of transmission angle data are stored, and the transmission angle can be more finely varied.

The delay period calculation unit 47 computes the delay time Δt based on Equation (1) above by using the inputted transmission angle data θs, the preset element pitch d of the ultrasonic elements 12, and the acoustic velocity c, and outputs the delay time Δt as a delay setting signal to the signal delay circuit 45.

The storage unit 48 is provided with a memory, hard disk, or other recording medium, for example, and readably stores various data and programs which are necessary in processing by the reception measuring unit 46, the delay period calculation unit 47, or the measurement control unit 49.

Specific examples of the various data mentioned above include position data of an ultrasonic array 11 in the probe 23, transmission angle data θs, and TOF data. The various programs are described in detail hereinafter, but are executed in the measurement control unit 49, and include a center position estimation program for estimating the center position of the blood vessel based on the TOF data, a reflection position coordinate computation program for computing the coordinate positions of six reflection positions of the blood vessel based on the TOF data, an outside diameter computation program for computing the outside diameter of the blood vessel and the center coordinates of the blood vessel from the coordinate positions of three reflection positions, an inside diameter computation program for computing the inside diameter of the blood vessel and the center coordinates of the blood vessel from the coordinate positions of three reflection positions, a warning output program for comparing the two center coordinates of the blood vessel and issuing a warning, and other programs.

Figure 9:
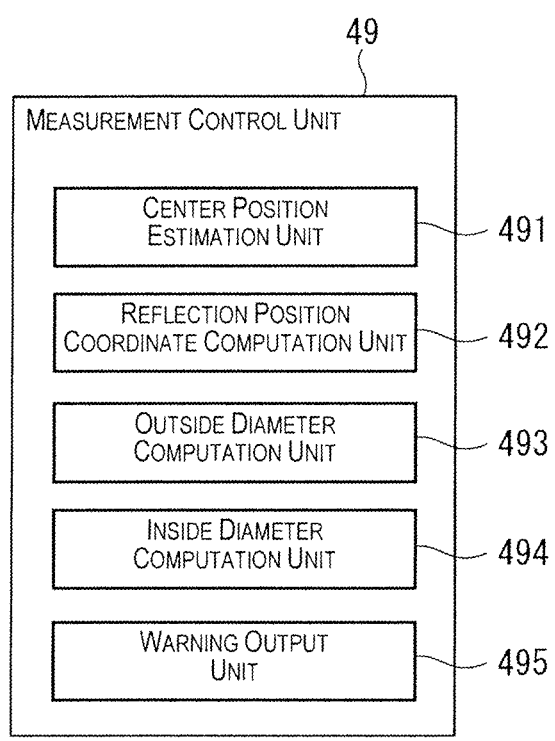
FIG. 9 is a block diagram showing the general configuration of the measurement control unit of the embodiment.

FIG. 9 is a block diagram showing the general configuration of the measurement control unit 49.

The measurement control unit 49 is provided with a central processing unit (CPU), for example, and executes programs stored in the storage unit 48. In other words, the measurement control unit 49 performs various functions by processing programs and data stored in the storage unit 48. The measurement control unit 49 thus configured processes the programs during measurement of the diameter of a blood vessel, and thereby realizes the center position estimation unit 491, a reflection position coordinate computation unit 492, an outside diameter computation unit 493, an inside diameter computation unit 494, and a warning output unit 495, as shown in FIG. 9.

The center position estimation unit 491 references the transmission angle data θs based on the two sets of TOF data of the reflected wave at the reflection position farthest from the inputted ultrasonic array 11, and the two sets of TOF data of the reflected wave at the reflection position nearest to the inputted ultrasonic array 11, estimates the center position of the blood vessel, and designates the estimated center position as the center estimate position.

The center position estimation unit 491 computes the transmission angle θs so that an ultrasonic wave is transmitted to the center estimate position from the ultrasonic array 11 other than the two ultrasonic arrays 11 already driven, and inputs the transmission angle data θs to the delay period calculation unit 47.

The reflection position coordinate computation unit 492 computes the distance from the ultrasonic arrays 11 to six reflection positions (A1, A2, B1, B2, C1, C2 in FIG. 8) based on the inputted TOF data of the first and third waves. Based on the transmission angle data stored in the storage unit 48, the six coordinate positions are computed by using Equations (3) through (8) below, where the origin is the position of the ultrasonic array 11B, and P is the arrangement interval of the ultrasonic arrays 11.

Equations (3) to (8)

$$A1(X, Y) = \left(c \cdot \frac{t1}{2} \cdot \sin\theta_a, c \cdot \frac{t1}{2} \cdot \cos\theta_a - P\right) \quad (3)$$

$$A2(X, Y) = \left(c \cdot \frac{t3}{2} \cdot \sin\theta_a, c \cdot \frac{t3}{2} \cdot \cos\theta_a - P\right) \quad (4)$$

$$B1(X, Y) = \left(c \cdot \frac{t1}{2} \cdot \sin\theta_b, c \cdot \frac{t1}{2} \cdot \cos\theta_b\right) \quad (5)$$

$$B2(X, Y) = \left(c \cdot \frac{t3}{2} \cdot \sin\theta_b, c \cdot \frac{t3}{2} \cdot \cos\theta_b\right) \quad (6)$$

$$C1(X, Y) = \left(c \cdot \frac{t1}{2} \cdot \sin\theta_c, P - c \cdot \frac{t1}{2} \cdot \cos\theta_c\right) \quad (7)$$

$$C2(X, Y) = \left(c \cdot \frac{t3}{2} \cdot \sin\theta_c, P - c \cdot \frac{t3}{2} \cdot \cos\theta_c\right) \quad (8)$$

The outside diameter computation unit 493 computes the outside diameter R of the blood vessel and computes the center coordinates O (x, y) by using Equation (9) below, based on the coordinate positions of A1, B1, C1 among the six reflection positions.

Equation (9)

$$\left(\frac{R}{2}\right)^2 = \left(c \cdot \frac{t1}{2} \cdot \sin\theta_a - x\right)^2 + \left(c \cdot \frac{t1}{2} \cdot \cos\theta_a - P - y\right)^2 = \quad (9)$$
$$\left(c \cdot \frac{t1}{2} \cdot \sin\theta_b - x\right)^2 + \left(c \cdot \frac{t1}{2} \cdot \cos\theta_b - y\right)^2 =$$
$$\left(c \cdot \frac{t1}{2} \cdot \sin\theta_c - x\right)^2 + \left(P - c \cdot \frac{t1}{2} \cdot \cos\theta_c - y\right)^2$$

The inside diameter computation unit 494 computes the inside diameter r of the blood vessel and computes the center coordinates O (x, y) by using Equation (10) below, based on the coordinate positions of A2, B2, C2 among the six reflection positions.

Equation (10)

$$\left(\frac{r}{2}\right)^2 = \left(c \cdot \frac{t3}{2} \cdot \sin\theta_a - x\right)^2 + \left(c \cdot \frac{t3}{2} \cdot \cos\theta_a - P - y\right)^2 = \quad (10)$$
$$\left(c \cdot \frac{t3}{2} \cdot \sin\theta_b - x\right)^2 + \left(c \cdot \frac{t3}{2} \cdot \cos\theta_b - y\right)^2 =$$
$$\left(c \cdot \frac{t3}{2} \cdot \sin\theta_c - x\right)^2 + \left(P - c \cdot \frac{t3}{2} \cdot \cos\theta_c - y\right)^2$$

The warning output unit 495 compares the offset amount of the two sets of center coordinates computed by the outside diameter computation unit 493 and the inside diameter computation unit 494 with a predetermined threshold value. In the case that the offset amount exceeds the threshold value, the warning output unit 495 issues a warning instructing the user to reattach the probe 23 in the test position to a display unit (not shown) of the device body 2.

The warning output unit 495 compares the offset amount of the two sets of center coordinates computed by the outside diameter computation unit 493 and the inside diameter computation unit 494, and the center estimate position of the blood vessel estimated by the center position estimation unit 491. In the case that the offset amount exceeds the threshold value, a warning instructing the user to reattach the probe 23 in the test position is issued to a display unit (not shown) of the device body 2.

3. Measurement Processing of Blood Vessel Diameter Measurement Device

Figure 10:
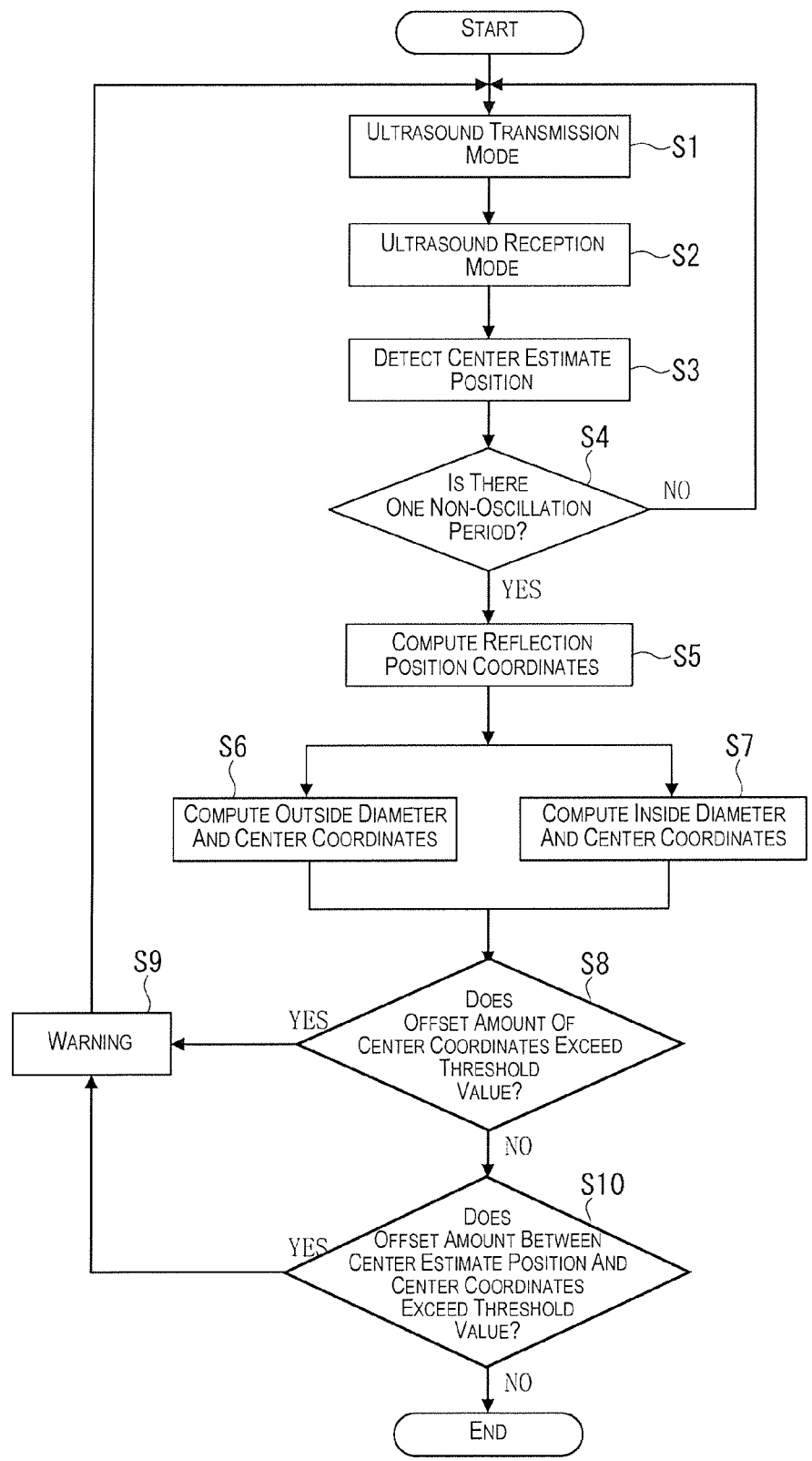
FIG. 10 is a flowchart showing the measurement processing of the blood vessel diameter measurement device of the embodiment.

The measurement processing of the blood vessel diameter measurement device 1 will next be described with reference to the flowchart shown in FIG. 10.

First, the probe 23 of the blood vessel diameter measurement device 1 is appressed to an arm, for example, or other test position of a living body, and the band is tightened to fix the device body 2 in the test position.

The user then operates the operating unit, whereby an input signal is inputted, whereupon the blood vessel diameter measurement device 1 begins measuring the diameter of a blood vessel.

The measurement control unit 49 then performs processing for switching to a state in which two ultrasonic arrays 11 can be driven. Here, the measurement control unit 49 outputs a switching control signal indicating a switch to a state in which two ultrasonic arrays 11 can be driven to the ultrasonic array switching circuit 41.

The measurement control unit 49 then performs various processing in the ultrasonic wave transmission mode (step S1).

In this ultrasonic wave transmission mode, the measurement control unit 49 reads the transmission angle data θs from the storage unit 48 and outputs the transmission angle data θs to the delay period calculation unit 47. The transmission angle data θ1 is read first and outputted to the delay period calculation unit 47. The delay period calculation unit 47 thereby computes the delay time Δt based on Equation (1) and outputs the result as a delay setting signal to the signal delay circuit 45.

When the measurement control unit 49 inputs a control signal indicating a switch to the ultrasonic wave transmission mode from the measurement control unit 49 to the ultrasound mode switching control unit 43, in the ultrasound signal transmission circuit 44, drive signals (drive pulses) for output to the ultrasonic elements 12 of two ultrasonic arrays 11 is outputted to the signal delay circuit 45. In the signal delay circuit 45, a delay setting signal is inputted from the delay period calculation unit 47 as described above. The drive signals are therefore delayed by a delay time based on the delay setting signal and outputted to the reception/transmission switching circuit 42.

The reception/transmission switching circuit 42 then outputs the drive signals inputted from the signal delay circuit 45 to the ultrasonic array switching circuit 41.

The reception/transmission switching circuit 42 is switched by a control signal inputted from the ultrasound mode switching control unit 43 to a state in which the drive signals inputted from the signal delay circuit 45 are outputted to the ultrasonic array switching circuit 41, as described above. The delayed drive signals outputted from the signal delay circuit 45 are therefore outputted to the ultrasonic elements 12 of the two ultrasonic arrays 11 via the ultrasonic array switching circuit 41.

By the operation described above, ultrasonic waves are outputted from the two ultrasonic arrays 11 at a transmission angle corresponding to the transmission angle data θ1. By performing the processing described above for the transmission angle data θ2 through θ5 as well, ultrasonic waves are outputted from the two ultrasonic arrays 11 at transmission angles corresponding to the transmission angle data θ1 through θ5.

The reception measuring unit 46 performs processing whereby the ultrasound mode switching control unit 43 switches to the reception mode, and when a reception signal corresponding to a reflected ultrasonic wave received by an ultrasonic array 11 is inputted from the reception/transmission switching circuit 42 to the reception measuring unit 46, the time is acquired at the timing of the input. The ultrasound mode switching control unit 43 then performs the various processing of the ultrasonic wave reception mode after the time taken for a 1 to 2-cycle burst wave to be outputted, for example (step S2).

In the ultrasonic wave reception mode of step S2, the ultrasound mode switching control unit 43 outputs a control signal instructing the reception/transmission switching circuit 42 to output the reception signal, inputted from the ultrasonic array switching circuit 41, to the reception measuring unit 46.

An ultrasonic wave is thereby received by the ultrasonic array 11, and when a reception signal is inputted from the ultrasonic array switching circuit 41 to the reception/transmission switching circuit 42, the reception signal is outputted to the reception measuring unit 46.

The reception measuring unit 46 monitors the time counted by the clock unit, acquires the TOF data, which is the time from the timing of reception of the ultrasonic wave until the timing at which the reception signal is inputted, and outputs the TOF data to the measurement control unit 49. The measurement control unit 49 then stores the inputted TOF data in an appropriately readable form in the storage unit 48.

The TOF data stored in the storage unit 48 in this instance are the two sets of TOF data of the reception signal for which inputting is last to be completed among the reception signals of the reflected waves transmitted for each transmission angle (transmission angles θ1 through θ5 shown in FIG. 5, for example) from two ultrasonic arrays 11 and reflected by the blood vessel, and the two sets of TOF data of the reception signal of the reflected wave first to be reflected, as described above.

The center position estimation unit 491 of the measurement control unit 49 then reads the TOF data and the like from the storage unit 48, estimates the center position of the blood vessel, and designates the estimated center position as the center estimate position (step S3). The center position estimation unit 491 then computes the transmission angle θs so that an ultrasonic wave is transmitted to the center estimate position from the ultrasonic array 11 other than the two ultrasonic arrays 11 already driven, and inputs the transmission angle data θs to the delay period calculation unit 47.

The remaining ultrasonic array 11 then transmits ultrasonic waves at the computed transmission angle θs, and the reception measuring unit 46 acquires the TOF data of the first wave and third wave of the reflected waves of the ultrasonic waves, and inputs the TOF data to the measurement control unit 49. The measurement control unit 49 stores the inputted TOF data in an appropriately readable form in the storage unit 48.

The reception measuring unit 46 determines whether a non-oscillation period is present between reception of the reception signal of the first wave and the reception signal of the third wave of the reflected waves (step S4). When at least one non-oscillation period is present, noise or other effects are determined to be absent, and the processing of the next step S5 is executed.

In the case that there is no non-oscillation period (i.e., the reception signal continues to be received), the reception measuring unit 46 determines that noise or other effects are present, the process returns to step S1, and the measurement control unit 49 performs various processing in the ultrasonic wave transmission mode. When a non-oscillation period is determined to be absent despite performing the processing from step S1 to step S4 a predetermined number of times, the measurement control unit 49 performs processing for outputting an error message instructing the user to reattach the probe 23.

The reflection position coordinate computation unit 492 of the measurement control unit 49 then performs processing for computing the coordinate positions of the reflection positions (step S5).

The reflection position coordinate computation unit 492 reads the TOF data or the like from the storage unit 48, and computes the coordinate positions of the six reflection positions A1, A2, B1, B2, C1, C2 shown in FIG. 8, by using Equations (3) through (8) described above.

The outside diameter computation unit 493 then computes the outside diameter R of the blood vessel and the center coordinates O (x, y) of the blood vessel by using the coordinate positions of the reflection positions A1, B1, C1 computed in step S5, and Equation (9) described above (step S6).

The inside diameter computation unit 494 also computes the inside diameter r of the blood vessel and the center coordinates O (x, y) of the blood vessel by using the coordinate positions of the reflection positions A2, B2, C2 computed in step S5, and Equation (10) described above (step S7).

The warning output unit 495 then compares the offset amount of the center coordinates O computed in steps S6 and S7 with a predetermined threshold value (step S8). In the case that the offset amount of the center coordinates O is greater than the predetermined threshold value, a warning is issued which instructs the user to reattach the probe 23 in the test position (step S9), the process returns to step S1, and measurement is started again.

In the case that the offset amount of the center coordinates O is less than the predetermined threshold value, the offset amount between the center coordinates O and the estimated center position is compared with a predetermined threshold value (step S10). In the case that the offset amount is less than the threshold value, the processing for measuring the diameter of the blood vessel is ended. In the case that the offset amount is greater than the threshold value, the warning output unit 495 issues the warning of step S9, the process returns to step S1, and measurement is started again.

4. Operational Effects of Present Embodiment

In the present embodiment, since the signal delay circuit 45 is provided for controlling the transmission angle of the ultrasonic waves so that the ultrasonic waves pass through the center O of the blood vessel, the ultrasonic waves can be reliably transmitted in the direction orthogonal to the wall surface of the blood vessel, the intensity of the reflected waves can be prevented from decreasing as in the conventional technique described above, and the reflected waves can be reliably received.

The reception measuring unit 46 is also provided for measuring, as the third wave, the reflected wave that arrives within the range of the predetermined time T of Equation (2) above from the first wave for which the time to reception is shortest after transmission of the ultrasonic waves. Specifically, by providing the reception measuring unit 46, the second and fourth waves reflected by the inside wall of the blood vessel subsequently to the first wave can be excluded, and the first wave and the third wave, which is received within the range of the predetermined time T, can be reliably received distinctly from each other. The TOF data of the reception signal of the third wave can thereby be accurately acquired, and the coordinates of the reflection positions A2, B2, C2 of the ultrasonic waves in the blood vessel can be accurately calculated by using Equations (4), (6), and (8). Consequently, the outside diameter R, the inside diameter r, and the center coordinates O of the blood vessel can be computed more accurately by the outside diameter computation unit 493 and the inside diameter computation unit 494 by using Equations (9) and (10).

Furthermore, since the reception measuring unit 46 determines whether there is at least one non-oscillation period between the first wave and the third wave, it is possible to detect a reflected wave in which the third wave is continuous from the first wave, for example. Consequently, in the case that the reflected waves are continuous waves, by performing another measurement, the reflection position of the first wave and the reflection position of the third wave can be reliably specified, and the diameter of the blood vessel can be accurately measured.

The warning output unit 495 is also provided for comparing the offset amount of the center coordinates O computed by the outside diameter computation unit 493 and the inside diameter computation unit 494 with a predetermined threshold value, and the warning output unit 495 outputs a warning instructing the user to reattach the probe 23 in the case that the offset amount exceeds the threshold value. Through this configuration, another measurement is performed after the user reattaches the probe 23 in the test position, and the offset amount of the center coordinates O is less than the threshold value. The center coordinates O of the blood vessel can thereby be calculated more accurately, and the diameter of the blood vessel can be accurately measured.

Furthermore, the warning output unit 495 compares the offset amount of the center estimate position of the blood vessel estimated by the center position estimation unit 491 and the center coordinates O computed by the outside diameter computation unit 493 and the inside diameter computation unit 494, and outputs a warning instructing the user to reattach the probe 23 in the case that the offset amount exceeds the threshold value. By then performing another measurement, the center coordinates of the blood vessel can be calculated more accurately, and the diameter of the blood vessel can be accurately measured.

Modifications of Embodiment

The present invention is not limited to the embodiment described above, and modifications, improvements, and the like in a range in which the objects of the present invention can be achieved are included within the scope of the present invention.

In the embodiment described above, the center position of the blood vessel is estimated based on two reflected waves of the ultrasonic waves that are transmitted from two ultrasonic arrays 11, but the center position of the blood vessel may also be estimated based on three reflected waves from the reflected waves of the ultrasonic waves transmitted from three ultrasonic arrays 11. In this case, the center position can be estimated with greater precision than in the case of estimating the center position of the blood vessel by using two ultrasonic arrays 11.

In the embodiment, described above, a blood vessel diameter measurement device 1 is described which uses three ultrasonic arrays 11, but this configuration is not limiting, and four or more ultrasonic arrays 11 may be used.

In the embodiment described above, the open parts 101 are circular in plan view, but this configuration is not limiting, and the open parts 101 may be formed in a rectangular or other shape according to the flexure balance of the diaphragms 13 or the stability with which the diaphragms 13 are vibrated by the piezoelectric bodies 14. Specifically, the ultrasonic elements 12 may be designed in any shape, while taking into consideration the balance of stress and other factors during vibration of the diaphragms 13.

In the embodiment described above, an example is described in which ultrasonic waves are both transmitted and received by the ultrasonic elements 12 in the ultrasonic arrays 11, and the ultrasound mode switching control unit 43 switches between an ultrasonic wave transmission mode and an ultrasonic wave reception mode, but this configuration is not limiting, and ultrasonic elements dedicated for reception and ultrasonic elements dedicated for transmission may be provided in a parallel configuration.

In the embodiment described above, an example is described in which the delay period calculation unit 47 is a device for calculating the delay time of the drive signal inputted to the ultrasonic elements 12, by acquiring acquires transmission angle data from the measurement control unit 49. In other words, an example is described in which the delay period calculation unit 47 is configured as hardware. However, this configuration is not limiting. For example, a configuration may be adopted in which a delay time calculation program is stored in the storage unit 48, the delay time calculation program is read and executed by the measurement control unit 49, and the delay time is thereby calculated in each drive signal.

In the embodiment described above, an example is described in which the measurement control unit 49 reads and executes various programs as the center position estimation unit 491, the reflection position coordinate computation unit 492, the outside diameter computation unit 493, the inside diameter computation unit 494, and the warning output unit 495. However, the center position estimation unit 491, the reflection position coordinate computation unit 492, the outside diameter computation unit 493, the inside diameter computation unit 494, and the warning output unit 495, for example, may also be configured as hardware using an IC or other integrated circuit, for example.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A blood vessel diameter measurement device comprising:
at least three ultrasonic arrays arranged on a probe configured and arranged to touch a living body, each of the ultrasonic arrays having a linear array structure in which a plurality of ultrasonic elements are arranged apart from each other with a first pitch in a single direction, the ultrasonic arrays being arranged such that the ultrasonic arrays have a same single scan plane and being arranged, in the single direction, apart from each other with a second pitch that is greater than the first pitch; and
a central processing unit computing at least one of an outside diameter and an inside diameter of a blood vessel in the living body based on an arrival time between transmission of ultrasonic waves from the ultrasonic arrays and arrival of the ultrasonic waves at the ultrasonic arrays after the ultrasonic waves are reflected by the blood vessel,
each of the ultrasonic arrays transmitting the ultrasonic waves from the plurality of ultrasonic elements by delaying transmitting timings of the ultrasonic waves to have a transmission angle of the ultrasonic waves such that the ultrasonic waves pass through a center of the blood vessel,
each of the ultrasonic arrays receiving a first reflected wave at a first arrival time and a second reflected wave at a second arrival time after the first arrival time within a range of a predetermined time,
the central processing unit computing at least one of the outside diameter of the blood vessel based on the first arrival time for each of the ultrasonic arrays and the inside diameter of the blood vessel based on the second arrival time for each of the ultrasonic arrays,
the central processing unit computing at least one of the outside diameter and the inside diameter of the blood vessel further based on the second pitch of the ultrasonic arrays.

2. The blood vessel diameter measurement device according to claim 1, wherein
the central processing unit estimates a center position of the blood vessel based on a most-delayed arrival time of a most-delayed reflected wave among reflected waves of the ultrasonic waves transmitted from at least two of the ultrasonic arrays at different transmission angles and reflected by the blood vessel, and based on the transmission angle corresponding to the most-delayed reflected wave.

3. The blood vessel diameter measurement device according to claim 1, wherein
the central processing unit computes center coordinates of the blood vessel based on coordinates of a reflection position of the first reflected wave for each of the ultrasonic arrays, computes the center coordinates of the blood vessel based on coordinates of a reflection position of the second reflected wave for each of the ultrasonic arrays, determines whether an offset amount between the center coordinates based on coordinates of the reflection position of the first reflected wave for each of the ultrasonic arrays and the center coordinates based on coordinates of the reflection position of the second reflected wave for each of the ultrasonic arrays exceeds a predetermined threshold value, and outputs a warning when the offset amount exceeds the threshold value.

4. The blood vessel diameter measurement device according to claim 1, wherein
the central processing unit computes center coordinates of the blood vessel based on coordinates of a reflection position of the first reflected wave for each of the ultrasonic arrays, computes the center coordinates of the blood vessel based on coordinates of a reflection position of the second reflected wave for each of the ultrasonic arrays, and
the central processing unit further estimates a center position of the blood vessel based on a most-delayed arrival time of a most-delayed reflected wave among the reflected waves of the ultrasonic waves transmitted from at least two of the ultrasonic arrays at different transmission angles and reflected by the blood vessel, and based on the transmission angle corresponding to the most-delayed reflected wave, and based on the transmission angle corresponding to the latest-arriving reflected wave, determines whether an offset amount between the center position of the blood vessel that has been estimated and the center coordinates that has been computed exceeds a predetermined threshold value, and outputs a warning when the offset amount exceeds the threshold value.

5. The blood vessel diameter measurement device according to claim 1, wherein
the central processing unit excludes reception of a reflected wave reaching each of the ultrasonic arrays at a time other than the range of the predetermined time after the first reflected wave has been received and before the predetermined time starts.

6. A blood vessel diameter measurement device comprising:
at least three ultrasonic arrays arranged on a probe configured and arranged to touch a living body, each of the ultrasonic arrays having a linear array structure in which a plurality of ultrasonic elements are arranged in a single direction, the ultrasonic arrays being arranged such that the ultrasonic arrays have a same single scan plane; and
a central processing unit computing at least one of an outside diameter and an inside diameter of a blood vessel in the living body based on an arrival time between transmission of ultrasonic waves from the ultrasonic arrays and arrival of the ultrasonic waves at the ultrasonic arrays after the ultrasonic waves are reflected by the blood vessel,
each of the ultrasonic arrays transmitting the ultrasonic waves from the plurality of ultrasonic elements by delaying transmitting timings of the ultrasonic waves to have a transmission angle of the ultrasonic waves such that the ultrasonic waves pass through a center of the blood vessel, each of the ultrasonic arrays receiving a first reflected wave at a first arrival time and a second reflected wave at a second arrival time after the first arrival time within a range of a predetermined time, the central processing unit computing at least one of the outside diameter of the blood vessel based on the first arrival time for each of the ultrasonic arrays and the inside diameter of the blood vessel based on the second arrival time for each of the ultrasonic arrays, the central processing unit determining whether there is at least one non-oscillation period of a reflected wave between the first reflected wave and the second reflected wave.

7. The blood vessel diameter measurement device according to claim 6, wherein the central processing unit excludes reception of a reflected wave reaching each of the ultrasonic arrays at a time other than the range of the predetermined time after the first reflected wave has been received and before the predetermined time starts.

8. A blood vessel diameter measurement method comprising:

transmitting ultrasonic waves from a plurality of ultrasonic elements of each of at least three ultrasonic arrays by delaying transmitting timings of the ultrasonic waves to have a transmission angle of the ultrasonic waves such that the ultrasonic waves pass through a center of a blood vessel, the at least three ultrasonic arrays being arranged on a probe configured and arranged to touch a living body, each of the ultrasonic arrays having a linear array structure in which the plurality of the ultrasonic elements are arranged apart from each other with a first pitch in a single direction, the ultrasonic arrays being arranged such that the ultrasonic arrays have a same single scan plane and being arranged, in the single direction, apart from each other with a second pitch that is greater than the first pitch;

receiving a first reflected wave at a first arrival time and a second reflected wave at a second arrival time after the first arrival time within a range of a predetermined time; and computing at least one of the outside diameter of the blood vessel based on the first arrival time for each of the ultrasonic arrays and the inside diameter of the blood vessel based on the second arrival time for each of the ultrasonic arrays, the computing including computing the at least one of the outside diameter and the inside diameter of the blood vessel further based on the second pitch of the ultrasonic arrays.

9. The blood vessel diameter measurement method according to claim 8, further comprising estimating a center position of the blood vessel based on a most-delayed arrival time of a most-delayed reflected wave among reflected waves of the ultrasonic waves transmitted from at least two of the ultrasonic arrays at different transmission angles and reflected by the blood vessel, and based on the transmission angle corresponding to the most-delayed reflected wave.

10. The blood vessel diameter measurement method according to claim 8, further comprising determining whether there is at least one non-oscillation period of a reflected wave between the first reflected wave and the second reflected wave.

11. The blood vessel diameter measurement method according to claim 8, further comprising computing center coordinates of the blood vessel based on coordinates of a reflection position of the first reflected wave for each of the ultrasonic arrays, computing the center coordinates of the blood vessel based on coordinates of a reflection position of the second reflected wave for each of the ultrasonic arrays, determining whether an offset amount between the center coordinates based on coordinates of the reflection position of the first reflected wave for each of the ultrasonic arrays and the center coordinates based on coordinates of the reflection position of the second reflected wave for each of the ultrasonic arrays exceeds a predetermined threshold value, and outputting a warning when the offset amount exceeds the threshold value.

12. The blood vessel diameter measurement method according to claim 8, further comprising computing center coordinates of the blood vessel based on coordinates of a reflection position of the first reflected wave for each of the ultrasonic arrays, computing the center coordinates of the blood vessel based on coordinates of a reflection position of the second reflected wave for each of the ultrasonic arrays, estimating a center position of the blood vessel based on a most-delayed arrival time of a most-delayed reflected wave among the reflected waves of the ultrasonic waves transmitted from at least two of the ultrasonic arrays at different transmission angles and reflected by the blood vessel, and based on the transmission angle corresponding to the most-delayed reflected wave, and based on the transmission angle corresponding to the latest-arriving reflected wave, determining whether an offset amount between the center position of the blood vessel that has been estimated and the center coordinates that has been computed exceeds a predetermined threshold value, and outputting a warning when the offset amount exceeds the threshold value.

13. The blood vessel diameter measurement method according to claim 8, further comprising excluding reception of a reflected wave reaching each of the ultrasonic arrays at a time other than the range of the predetermined time after the first reflected wave has been received and before the predetermined time starts.

* * * * *